United States Patent

Newman et al.

[11] Patent Number: 6,035,276
[45] Date of Patent: Mar. 7, 2000

[54] MEDICAL PRACTITIONER CREDENTIALING SYSTEM

[75] Inventors: Iris Newman, Philadelphia; Thomas McSweeney, Jr., Drexel Hill, both of Pa.

[73] Assignee: Veritas Medical Services, Inc., Philadephia, Pa.

[21] Appl. No.: 08/953,440

[22] Filed: Oct. 17, 1997

[51] Int. Cl.[7] .................................................. G06F 17/60
[52] U.S. Cl. .................. 705/2; 705/3; 707/505; 707/506
[58] Field of Search ................. 705/1, 2, 26, 4, 705/3; 707/104, 505, 506, 507, 508

[56] References Cited

U.S. PATENT DOCUMENTS

| | | | |
|---|---|---|---|
| 4,858,121 | 8/1989 | Barber et al. ............................ | 705/2 |
| 5,070,452 | 12/1991 | Doyle et al. . | |
| 5,272,623 | 12/1993 | Grubb et al. ............................ | 395/701 |
| 5,325,478 | 6/1994 | Shelton et al. ......................... | 707/507 |
| 5,483,443 | 1/1996 | Milstein et al. ........................ | 705/3 |
| 5,644,778 | 7/1997 | Burks et al. ............................ | 705/2 |
| 5,664,109 | 9/1997 | Johnson et al. ........................ | 705/2 |
| 5,701,423 | 12/1997 | Crozier ................................... | 345/335 |
| 5,758,324 | 5/1998 | Hartman et al. ....................... | 705/1 |
| 5,787,434 | 7/1998 | Nakamura et al. .................... | 707/102 |

OTHER PUBLICATIONS

Slater, Pam, "Sacramento–Based Healthcheck Inc. Helps Consumers Check Up on Doctors", Sacramento Bee, Jul. 18, 1995.

"Equifax Enters Healthcare Information Field", PR Newswore, Mar. 15, 1995.

Smith, James M., "HHS' Doctor Database Draws Fire From Medical Lobby", Government Computer News, vol. 13, No. 21, Sep. 19, 1994.

Lipschultz, Seymour, Thory and Problems of Discrete Mathematics, McGraw–Hill, 1976.

Primary Examiner—Emanuel Todd Voeltz
Assistant Examiner—George D. Morgan
Attorney, Agent, or Firm—Lawrence G. Kurland, Esq.; Bryan Cave LLP

[57] ABSTRACT

A system and method for selectively generating provider application forms required to be submitted to health care provider organizations by physicians and related health care professionals. Physician credentialing profiles containing physician credentialing information are stored into a system database together with a plurality of different provider application formats associated with particular application forms which are completed selected data extracted from the common information contained in the stored physician credentialing profiles. The method automatically inputs a subset of physician credentialing information required by a particular selected provider application format into the provider application form associated with that format and generates the particular provider application form.

18 Claims, 2 Drawing Sheets

FIG. 1   VERI-FORM™ DATA FLOW DIAGRAM

6,035,276

MEDICAL PRACTITIONER CREDENTIALING SYSTEM

FIELD OF THE INVENTION

The present invention relates generally to physician credentialing and verification systems and, in particular, to systems capable of automatically generating a plurality of different insurance provider application forms in different formats based on a common set of physician credentialing information.

BACKGROUND OF THE INVENTION

Physician credentialing is the process that physicians, including other related health care professionals who must submit credentialing data, complete to become or remain affiliated with a particular health care provider organization (such as, for example, a managed health care group, a hospital or an insurance organization). Typically such physicians must complete an extensive application form and submit the completed form to the health care provider organization for review and acceptance. This process of completing and submitting application forms occurs both when the physician originally becomes affiliated with the health care provider organization and when the organization requires its affiliated physicians to re-credential themselves, i.e., re-submit their applications with up-to-date information. Currently, although the information required by each health care provider organization is generally similar in nature, each provider organization normally uses an application form customized to its own needs and requirements, in its own distinct format, and designed to elicit information that is important to that particular provider organization, which, as discussed below, often places an unnecessary and unwarranted ever increasing burden on the physician in today's health care environment, particularly if the physician is affiliated with several health care organizations.

Credentials verification is a related process whereby health care provider organizations verify the accuracy of the information contained in application forms submitted by physicians seeking appointment or re-appointment with the provider organization. Usually, to complete the credentials verification process, it is necessary to access several different sources to verify the information. Such sources may include, for example, state licensing boards, medical schools, the American Board of Medical Specialties, and the National Practitioner Data Bank. As required by governmental rules and regulations, each health care provider organization must individually and independently perform primary source verification and are prohibited from sharing the gathered information with other similarly situated provider organizations.

Currently, there are over 600,000 physicians in the United States, substantially all of whom are affiliated with a number of health care provider organizations. As the health care industry continues its current state of rapid expansion, new provider organizations are continuously entering the marketplace. It is not uncommon for physicians to service patients associated with several managed care organizations, be affiliated with more than one hospital, and interact with several insurance companies that insure their patients. Typically, physicians must be re-credentialed ever year or two by every organization with which they are affiliated. Thus, statistics show that, on average, each physician must complete and submit in the neighborhood of six application credentialing forms annually. While there have been some attempts to develop a standardized credentialing application format, these efforts have been largely unsuccessful. Because of the wide variety and number of formats, the process to complete all of the various forms is necessarily time consuming, inefficient, and labor intensive, particularly since these forms are generally manually completed due to the distinctions in format peculiar to each organization.

Thus, there is an ever increasing need to assist physicians and related health care professionals, as well as the organizations themselves that manage such professionals, with the completion of these credentialing application forms in a system which would allow physicians to automatically selectively generate a credentialing application tailored to a particular provider organization, from a plurality of different selectable choices in form and format, based upon a common set of pre-stored credentialing information about the physician. The preferred system would thus reduce the time and cost associated with the completion of these application forms and would help to minimize the possibility of errors contained in these forms.

Thus, the disadvantages of prior art credentialing systems are overcome by the present invention which is an automated system and method for selectively generating credentialing applications tailored to particular provider organizations.

SUMMARY OF THE INVENTION

The presently preferred method of the present invention comprises a method for selectively generating a plurality of different provider application forms based on a common set of physician credentialing information comprises the steps of storing a plurality of physician credentialing profiles containing physician credentialing information in a database, storing a plurality of different selectable provider application formats in a database requiring data which is a subset of the information stored in the physician credentialing profiles, automatically selectively inputting the subset of physician credentialing information required by a particular selectable provider application format into a provider application form, and generating the particular provider application form containing information inputted from the subset of stored physician credentialing information.

Preferably, the physician credentialing profiles are stored based on information provided by the physician on a universal application form that contains credentialing information regarding a particular physician. This universal application form may be completed in an number of ways including on a paper form, electronically and stored to a computer disk, or through an on-line service.

The presently preferred system of the present invention, which is intended to relieve practitioners, health care providers and organizations of the administrative burdens of completing different multiple forms associated with practitioner credentialing, comprises means for storing the plurality of physician credentialing profiles in the data base, means for storing the plurality of different provider application formats in the data base, means for automatically inputting the subset of physician credentialing information required by a particular provider application format into the provider application format, and means for generating the completed selected particular provider application form.

BRIEF DESCRIPTION OF THE DRAWING

These and other features, aspects, and advantages of the present invention will become better understood with regard to the following description, appended claims, and accompanying drawings.

DETAILED DESCRIPTION OF THE INVENTION

Figure 1:
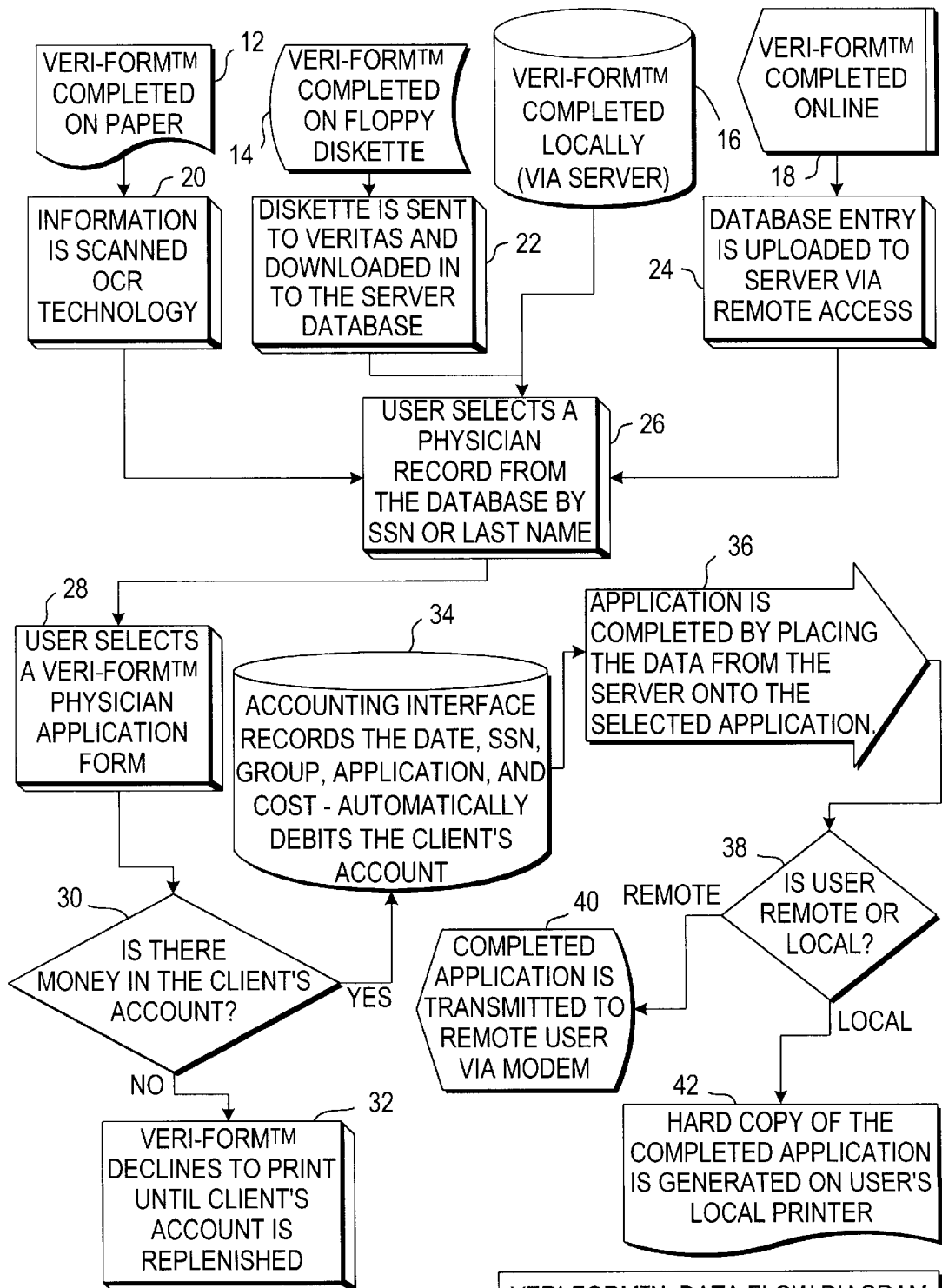
FIG. 1 is a high-level data flow diagram showing the major processing elements of, and flow of information through, the presently preferred physician credentialing process of the present invention.

The presently preferred method of the invention provides a method to electronically store a common set of credentialing information relating to physicians (and any other related health care professionals) who must have their credentials verified for use in automatically generating a plurality of different provider application forms having different formats. Preferably, the credentialing information related to a particular physician desiring to use the present invention is initially input in a common universal format, referred to as a universal application form, which the physician initially completes to use the system of the invention. Preferably, upon completion, the universal application form contains the biographical and statistical information in a common set of data which is usable for automatically preparing a plurality of different credentialing application forms in different associated formats. Typically, this common set of physician credentialing information includes the physician's name, address, practice specialties, appointment status, hospital associations, credentials (including educational background, internships, and residency programs), state licensing information, malpractice liability insurance information, and personal and professional references. In creating the common physician credentialing database, a separate universal application form is preferably completed for each physician or health care professional participating in, and using the benefits of, the system. The information on the universal application form is preferably provided to the common physician credentialing information database, which stores physician credentialing information related to each physician using the system. Preferably, the information is stored as a series of logically organized physician credentialing profiles and may be extracted as necessary to complete the various different selected provider application forms in the format associated with the selected application form.

The method of the present invention provides for several ways for physicians to initially complete a universal application form and have the information stored within the common physician credentialing information database. For example, the physician (or his or her staff) may manually complete a pre-printed universal application form. The form is then delivered to a credentialing managing organization, which loads the information into a physician credentialing information database (as a physician credentialing profile) residing on a conventional digital computer which has been conventionally programmed with software for carrying out the preferred method of the present invention, such as the software illustrated by the flow diagrams of FIGS. 1 and 2, and which may, by way of example, be written in Visual Basic or any other acceptable computer language for a WINDOWS operating system compatible with the conventional computer selected to run the software, such as an IBM THINKPAD. The credentialing managing organization is an entity responsible for managing the system, i.e., collecting physician credentialing information, creating electronic versions of provider application formats, completing selected provider application formats with selected physician credentialing information and generating a preferred provider application form in the associated format for use by the physician. Of course, portions (or all) of these steps may be accomplished by the physician or an independent physician association to which the physician belongs.

In another embodiment, a blank universal application form is stored on a conventional computer disk (or similar media) and the disk is sent to the physician. The physician, using a conventionally programmed digital computer, programmed with the software of the present invention, completes the universal application form and returns the disk (or its contents) to the credentialing managing organization. The physician may transmit the disk (or its contents) to the credentialing managing organization by any means including, for example, electronic mail, modem, or conventional mail services. The credentialing managing organization downloads and processes the contents of the universal application form in accordance with the software illustrated in the flow diagrams of FIGS. 1 and 2 and creates and stores a physician credentialing profile for that particular physician. Of course, an independent physician association may complete a number of universal application forms and conventionally store such forms on a single disk for each of the physicians affiliated with the association. This preferred embodiment thus automates the method of storing the physician credentialing information into the physician credentialing information database.

In yet another embodiment, the universal application form may be accessed via a conventional telecommunication link and the physician's credentialing information may be entered into the form and electronically transferred to the credentialing managing organization. The credentialing managing organization then receives the universal application form(s) and conventionally loads the information into the physician credentialing information database as one (or a set) of physician credentialing profiles.

Alternatively, the process of conventionally loading the database with physician credentialing profiles can be conventionally interfaced with an existing data base of physician information, eliminating the need for physicians or their associations to complete any application at all. In such an instance, the credentialing managing organization (or the independent physician association) would conventionally access the existing database and extract the information to build the physical credentialing information database.

Additionally, as shown and preferred, the preferred method of the present invention creates and stores a provider application database containing formats for each of the different provider application forms used by the various hospitals, health care management and other health care organizations to which the physicians may desire to apply for credentialing or re-credentialing. Preferably, this provider application database contains a unique entry or record for each of the various provider application forms, and each entry preferably conventionally has fields for each different category of information required to be provided on the application form. Each entry is conventionally logically connected to its corresponding category of information contained in the physician credentialing profiles.

Preferably, upon request from a physician or independent physician association, the system conventionally extracts the information contained in the physician credentialing profile relating to a particular selected physician and populates a provider application format corresponding to a particular selected provider organization to generate a provider application form. The particular physician and provider organization may be selected using any suitable conventional means. For example the physician credentialing profile for the particular physician may be conventionally found in the physician credentialing information database based on the physician's name, social security number(SSN), or any other appropriate physician or record discriminator. Similar record discriminators may be used to identify and locate the associated provider application format corresponding to the selected provider organization.

The completed provider application form may then be printed on a conventional printer, such as an HP LASER JET, and delivered to the physician, (or transferred electronically to the physician for printing on a conventional printer within the physician's office), reviewed, signed, and submitted to the appropriate health care provider organization.

Using the preferred version wherein the independent physician associations are electronically linked to the system databases (with or without using a credentialing managing organization), the physician association may conventionally download and print out a particular credentialing application form for one (or many) of its professionals in their own office, and, if desired, may conventionally network the software or use it as a stand-alone. Thus, using this preferred embodiment, the independent physician associations have virtually instant access to completed applications in different formats for a variety of different managed care organizations at significantly reduced cost and time. Preferably, for security reasons, each physician association's data conventionally resides in a separate directory within the system and can only be accessed using appropriate conventional screening procedures such as, for example, logon identification and password.

Periodically, the credentialing information provided by the physicians must be revised and updated to reflect any changes in the physician's credentialing status. These updates may be made using any of the previously defined methods to initially create a physician credentialing profile. For example, the physician may submit a new or revised uniform application form (either in hard copy or on a disk) to the credentialing managing organization and the managing organization then conventionally updates the appropriate entries in the physician credentialing information database. Alternatively, if the physicians (or their affiliated associations) have a conventional telecommunication interface to the system databases, preferably they will be able to conventionally add, edit, delete and view the credentialing information associated with their particular physician(s).

The system may further include the steps of authenticating a request from a physician or individual physician association prior to generating a provider application form. Thus, an account may be established for each physician or physician association, potentially including the deposit of fees. Upon receipt of a request for generation of an application, the system conventionally verifies that the account is in good standing. This embodiment is particularly useful for situations wherein the physician association remotely accesses the system and prints an application on its local printer. Thus, the system will automatically debit the appropriate account for each application printed by that association. When the prepaid account reaches a predetermined level, a message is preferably transmitted to the association notifying it that the account is low and must be replenished.

Referring now to FIG. 1, a high-level data flow diagram of the presently preferred control software, showing the major processing elements of, and flow of information through, the presently preferred physician credentialing method of the present invention, is illustrated. The credentialing process preferably begins by receiving physician credentialing information and storing credentialing profiles containing such information in a common physician credentialing information database contained within the system. The credentialing information may preferably be received in multiple formats, such as, for example, a uniform application form received by a credentialing managing organization in a hard copy or paper format 12, which is conventionally loaded into the database by, for example, conventional scanning in the hard copy uniform application form using conventional optical character recognition technology 20. Alternatively, the physician credentialing information may be received as soft copies of uniform application forms conventionally stored on a portable computer medium (e.g., a disk), which medium is then delivered to the credentialing managing organization and its contents conventionally downloaded into the database In another embodiment, the credentialing information is conventionally created and stored locally (i.e., at the physician's office) 16. In this embodiment, a conventional computer system having appropriate credentialing system software loaded thereon is located at the physician's office, rather than at the facilities of a credentialing managing organization. The computer system thus populates the physician credentialing profiles with the credentialing information to build the physician credentialing information database.

In yet another embodiment, the universal application form(s) containing physician credentialing information are completed for the physician (or for all of the physicians belonging to the same independent physician association) 18 and the electronic versions of the forms are transferred to the credentialing managing organization via a conventional telecommunication link (e.g., a modem or via the Internet or another similar dial-in telecommunication service) 24.

Preferably, after the physician credentialing information is loaded into the physician credentialing information database as physician credentialing profiles (using information derived from the universal application forms) and after the set of provider application formats have been loaded in a provider application database (not shown in FIG. 1), the system is capable of generating provider application forms. Preferably, a user (i.e., a physician or one of his staff) selects a particular physician from the common physician credentialing information database based on, for example, the name or social security number (SSN) of that particular physician 26. Next, as represented by reference numeral 28, the user selects one (or more) of the different selectable provider application formats corresponding to (or each of) the health care organizations with which the physician desires to become associated or re-accredited.

The process may include a conventional means for verifying that the physician (or the independent physician association with which he is affiliated) is in good standing with the credentialing managing organization 30. If not, then as is common in such conventional verification systems, the system declines to process the request 32. If the physician and/or his association is in good standing 34, the system preferably records certain information regarding the request such as, for example, the date of the request, the identification of the physician (SSN or name), the group (i.e., the independent physician association), and the cost of the request.

As represented by reference numeral 36, the selected provider application format is conventionally extracted from the provider application database and populated or completed with information from the selected physician credentialing profile to generate the particular provider application form which has been selected in the format associated with that form. The system then delivers the completed selected provider application form to the user. For example, as represented by reference numeral 40, the completed provider application form may be transmitted to the user via a telecommunication link and then the user may print the form 42. Alternatively, if the system is operating at the user's facility, the completed form may simply be printed on a local printer 42.

Figure 2:
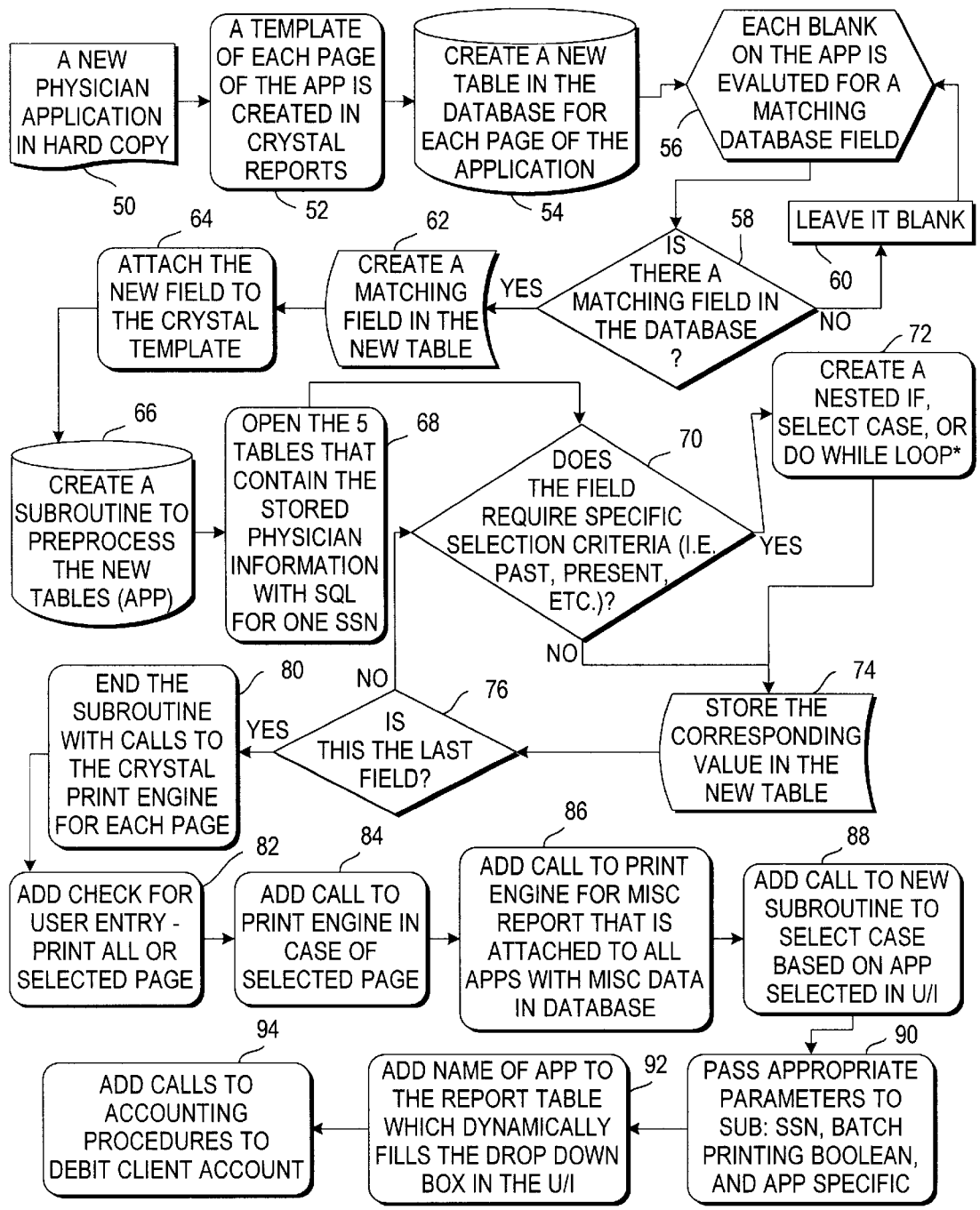
FIG. 2 is a more detailed high level data flow diagram of the system of FIG. 1, illustrating the presently preferred process of the present invention.

Referring now to FIG. 2, a more detailed data flow diagram of the control software of FIG. 1 for carrying out the presently preferred system and method of the present invention is shown. FIG. 2 illustrates in greater detail the processing of an application from hard copy to final result. As shown and preferred, a new physician application is provided in hard copy 50. A template is then created for each page of the application 52 in conventional software called Crystal Reports. A new table is then created in the data base for each page of the application 54. Each blank on the application is then evaluated for a matching data base field 56. A determination is then made as to whether or not there is a matching field in the data base 58. If not, then it is left blank 60. If the answer is YES, then a matching field is created in the new table 62. The new field is then attached to the Crystal Template 64. A subroutine is then created to preprocess the new tables (app) 66. The five tables that contain the stored physician information with SQL for one SSN is then opened 68. A determination is then made as to whether or not the field requires specific selection criteria, such as past, present, etc. 70. If the answer is YES, then a nested IF, SELECT CASE, or DO WHILE loop is created 72 and the corresponding value is then stored in the new table 74. If the answer is NO, then the system goes on to directly store the corresponding value in the new table 74. A determination is then made as to whether or not this is the last field 76. If the answer is NO, the system loops back to determine if the field requires specific selection criteria 70. If the answer is YES, the subroutine which calls to the conventional Crystal Print Engine for each page is then ended 80. A check is then added for user entry as to PRINT ALL or PRINT SELECTED PAGE 82. A call is then added to the Crystal Print Engine in case of PRINT SELECTED PAGE 84. A call is then added to the Crystal Print Engine for MISC REPORT that is attached to all applications with MISC DATA in the data base 86. A call is then added to the new subroutine to SELECT CASE based on the application selected 88. Appropriate parameters, such as SSN, BATCH PRINTING, BOOLEAN, and APPLICATION SPECIFIC, are then passed to a subroutine 90. The name of the application is then added to the Crystal Report Table which dynamically fills the drop down box on the computer screen 92. Calls are then added to Accounting Procedures to debit the client account 94.

The foregoing description merely illustrates the principles of the invention and it will be appreciated that those skilled in the art will be able to devise numerous arrangements which, although not explicitly shown or described herein, embody the principles of the present invention and are within the spirit and scope of the invention.

As shown by the description contained herein, the method of the present invention reduces the time, cost and risk of error involved in the repetitive task of completing many individualized application forms for credentialing and recredentialing of physicians and other health care professionals required by the various organizations with which they are, or desire to become, affiliated. Although the present invention has been described in considerable detail with reference to certain presently preferred versions thereof, other versions are possible without departing from the spirit and scope of the present invention.

We claim:

1. A method for selectively generating a provider application form from a plurality of selectable different provider application formats comprising the steps of:
    (a) generating credentialing profile information for a plurality of physicians in a common format and storing said information in a physician database, said physician database comprising a common data base source for said information for said plurality of selectable provider application formats;
    (b) storing a plurality of said different provider application formats in a provider database, said different provider application formats requiring data, said required data being a subset of the credentialing profile information for a selected physician stored in said physician database;
    (c) selecting a desired provider application format and automatically inputting the subset of credentialing profile information taken from said physician database for a selected physician required by said selected provider application format into a provider application form associated with said selected format; and
    (d) selectively generating the particular provider application form in said selected format, wherein the form includes information inputted from the subset of the stored physician credentialing information.

2. The method of claim 1 wherein the step of generating and storing a plurality of physician credentialing profiles comprises the steps of:
    (a) completing a plurality of universal application forms, wherein each universal application form contains the physician credentialing information about a particular physician; and
    (b) transferring the physician credentialing information contained on the plurality of universal application forms to said physician credentialing profiles in said physician database.

3. The method of claim 2 wherein the plurality of universal application forms are completed using an on-line telecommunication link and the physician credentialing profiles are stored based on received universal application forms.

4. The method of claim 1 wherein the plurality of physician credentialing profiles are stored based on information contained in an existing database of physician credentialing information.

5. The method of claim 1 wherein the step of storing provider application formats comprises the step of storing a unique entry for each of the plurality of provider application forms, each entry having fields for each of the subset of physician credentialing information required by that particular provider application form.

6. The method of claim 5 wherein each of said unique entries is logically connected to corresponding information contained in the physician credentialing profiles.

7. The method of claim 1 wherein the step of automatically inputting the subset of physician credentialing information further comprises the step of remotely accessing the plurality of physician credentialing profiles and the plurality of provider application formats to input the subset of physician credentialing information into a provider application form.

8. The method of claim 1 wherein the step of generating the particular provider application form further comprises the step of printing the provider application form.

9. The method of claim 1 wherein the step of generating the particular provider application form further comprises the step of electronically transmitting the provider application form.

10. A physician credentialing system comprising:
   (a) means for generating in a common format and storing a plurality of physician credentialing profiles in a physician database, the profiles comprising physician credentialing information each profile including the physician's name, address, practice specialties, appointment status, hospital associations, educational background, internships, and residency programs;
   (b) means for storing a plurality of different provider application formats in a provider database, the provider application formats requiring data, the required data being a subset of the credentialing profiling information for a selected physician stored in said physician database;
   (c) means for selecting a desired provider application format from said plurality of stored formats and for automatically inputting the subset of physician credentialing information required by said particular selected provider application format into a provider application form associated with said selected format; and
   (d) means for generating the selected particular provider application form, wherein the form includes information inputted from the subset of the stored physician credentialing information.

11. The physician credentialing system of claim 10 wherein the means for generating and storing a plurality of physician credentialing profiles comprises:
   (a) means for completing a plurality of universal application forms, wherein each universal application form contains the physician credentialing information about a particular physician; and
   (b) means for transferring the physician credentialing information contained on the plurality of universal application forms to physician credentialing profiles in said physician database.

12. The physician credentialing system of claim 11 wherein the means for completing a plurality of universal application forms comprises means for completing the forms using an on-line telecommunication link and wherein the physician credentialing profiles are stored based on received universal application forms.

13. The physician credentialing system of claim 10 wherein the means for storing the plurality of physician credentialing profiles comprises means for storing the profiles based on information contained in an existing database of physician credentialing information.

14. The physician credentialing system of claim 10 wherein the means for storing provider application formats comprises means for storing a unique entry for each of the plurality of provider application forms, each said entry having fields for each of the subset of physician credentialing information required by that particular provider application form.

15. The physician credentialing system of claim 14 wherein each said entry is logically connected to corresponding information contained in the physician credentialing profiles.

16. The physician credentialing system of claim 10 wherein the means for automatically inputting the subset of physician credentialing information further comprises means for remotely accessing the plurality of physician credentialing profiles and the plurality of provider application formats to input the subset of physician credentialing information into a provider application form.

17. The physician credentialing system of claim 10 wherein the means for generating the particular provider application form further comprises means for printing the provider application form.

18. The physician credentialing system of claim 10 wherein the means for generating the particular provider application form further comprises means for electronically transmitting the provider application form.

* * * * *